United States Patent [19] [11] 4,193,398
Refson [45] Mar. 18, 1980

[54] FLUID DISPLACEMENT
[75] Inventor: Bernard H. Refson, Truro, England
[73] Assignee: Watson-Marlow Limited, Falmouth, England
[21] Appl. No.: 909,453
[22] Filed: May 25, 1978
[51] Int. Cl.² .................... F24C 15/10; F24C 15/22
[52] U.S. Cl. .................... 128/213 R; 417/48; 128/260
[58] Field of Search .......... 128/260, 213 R, DIG. 12, 128/214 F; 417/48

[56] References Cited
U.S. PATENT DOCUMENTS

| | | | |
|---|---|---|---|
| 2,766,907 | 10/1956 | Wallace, Jr. | 128/DIG. 12 |
| 3,153,414 | 10/1964 | Beall et al. | 128/DIG. 12 |
| 3,645,111 | 2/1972 | Williamitis | 417/48 X |
| 3,760,804 | 9/1973 | Higuchi et al. | 128/260 |
| 3,760,805 | 9/1973 | Higuchi et al. | 128/260 |
| 4,033,345 | 7/1977 | Forenson et al. | 128/214 F |
| 4,041,944 | 8/1977 | Rhodes | 128/214 F |

Primary Examiner—Henry K. Artis

[57] ABSTRACT

An extracorporeal osmotic pump has a first chamber containing an osmotic fluid e.g. aqueous polyethylene glycol solution and a second chamber containing a weaker solution or solvent e.g. water. Between the two there is a duct containing the semipermeable membrane and nearer the first chamber one or more layers of porous material (e.g. four contiguous face-to-face discs of porous polyethylene) as a flow-control means.

12 Claims, 4 Drawing Figures

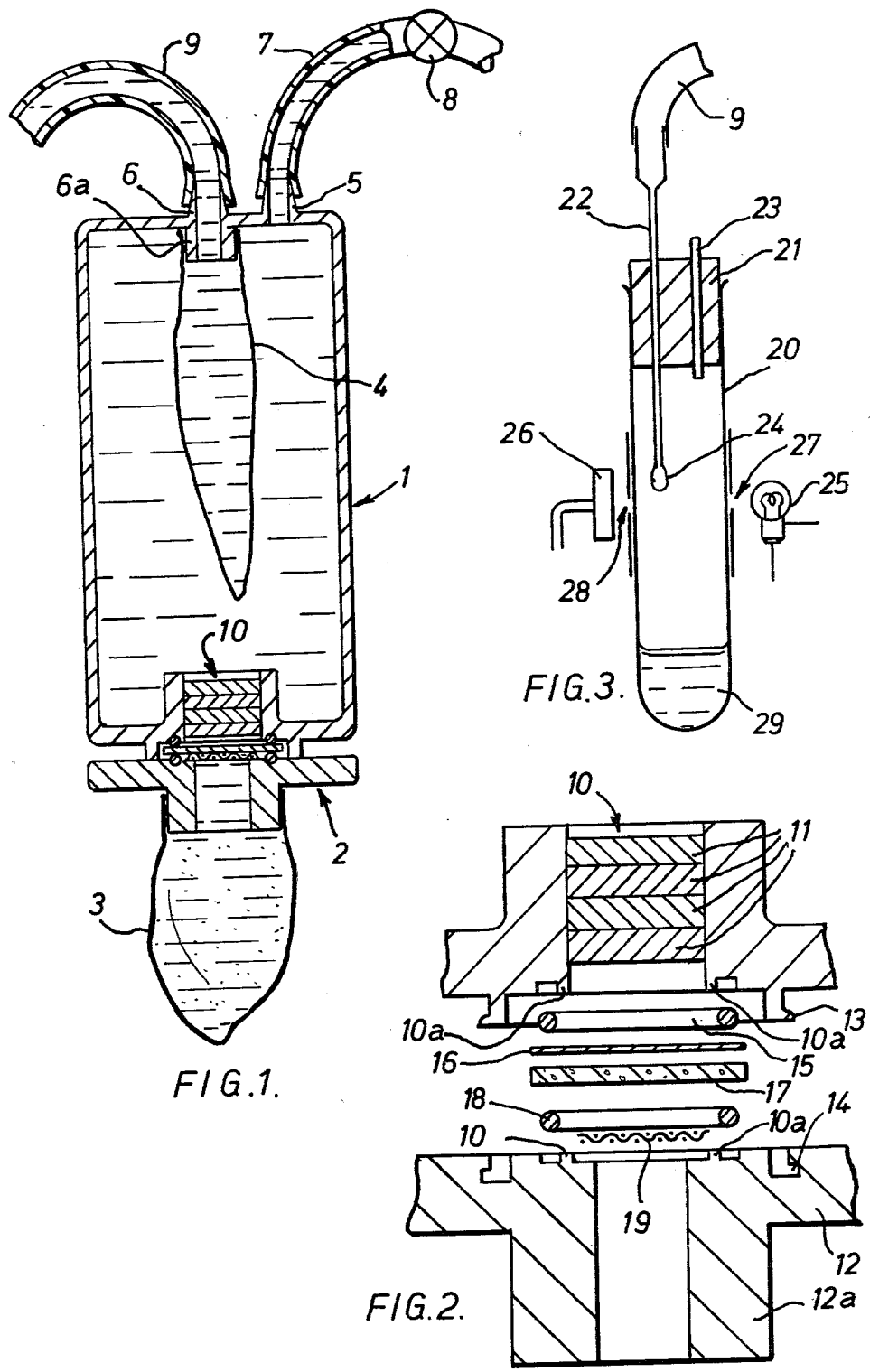

FLUID DISPLACEMENT

This invention relates to an osmotic pump, and especially to a design of osmotic pump capable of giving a generally constant flow rate over an extended period.

An osmotic pump is a device free from mechanically or electrically moving parts, typically used in a medical context for the incorporation of drugs or parenteral fluids into the system of a patient. A typical example of a material dispensed by such a pump is insulin, which can be dispensed into a diabetic patient for periods up to say 70 hours. Another example is heparin which is similarly dispensed into a patient with renal failure.

All osmotic pumps are based on the well known principle of osmosis, that is to say the one-way passage of solvent across a semi-permeable membrane from a weaker solution (or pure solvent) to a stronger solution.

Various designs have been proposed for converting the pressure generated by such a passage of liquid into a suitable motive power for dispensing materials into the system.

For instance, the intracorporeal device shown in U.S. Pat. No. 3,760,804 consists of a hollow container internally separated into two parts by a sliding separating wall. One part contains osmotic liquid, for example concentrated magnesium sulphate solution, and communicates to the surrounding body fluid environment (e.g. 0.9% saline) across a semi-permeable membrane. The other part contains the active agent formulation and communicates to the surrounding body fluid environment through a small orifice in a dispensing head. As liquid diffuses in through the semi-permeable membrane from the body fluid the sliding separating wall moves and forces the active agent formulation out of the orifice.

Another typical intracorporeal design is shown in U.S. Pat. No. 3,760,805. It consists generally of a liquid-permeable rigid external container enclosing two flexible bags. One such bag is sealed, contains osmotic fluid such as magnesium sulphate solution, and is made of, or coated or lined with, the semi-permeable membrane so as to be liquid-permeable. The other such bag is impermeable, contains active agent formulation and communicates with the exterior through a neck or orifice. In a body fluid environment the bag containing osmotic fluid swells and compresses the other bag to expel the active agent.

In all osmotic pumps the liquid diffusing inwards dilutes the internal osmotic fluid. This leads to a change of concentration, which in turn changes the flow rate. Typically, unless some expedient is adopted to control this change in flow rate, the pump dispenses more and more slowly with elapsing time. The phenomenon is rather more complex than can be totally explained merely by the dilution effect, and this point is discussed in more detail below.

One way of overcoming this tendency is to use a saturated solution of osmotic fluid also containing a further solute which dissolves in the incoming liquid, to maintain saturation. Because the osmotic fluid is always saturated the flow rate is stated to be constant. Thus, the devices shown in both U.S. Pat. Nos. 3,760,804 and 3,760,805, discussed above both envisaged the presence of magnesium sulphate crystals in the osmotic fluid chamber, for this purpose.

Another way of controlling the flow rate is stated to be to utilise a relatively long delivery duct from the active agent chamber. Thus, the Journal of Medical Engineering and Technology, September 1977, Page 282, shows an intracorporeal device with a tube extending along its axis from the dispensing orifice to the active agent chamber, the stated function of this tube being given on Page 281 as a "flow moderator".

The present invention provides a further method of controlling flow-rate e.g. to a uniform value, of a special utility in design of an extracorporeal injection device, which utilises a porous flow-controlling layer in combination with the semi-permeable membrane.

In one aspect therefore the invention consists in an osmotic pump wherein a semi-permeable membrane is associated with a layer of liquid permeable porous material on the side of the osmotically stronger solution, as a flow control means.

This layer may be contiguous with, but is more preferably spaced from the semi-permeable membrane.

In another aspect the invention consists in an extracorporeal osmotic pump comprising a first chamber for containing an osmotically stronger solution and a second chamber for containing an osmotically weaker solution or pure solvent, the two chambers communicating by a duct containing a semi-permeable membrane nearer the second chamber and a layer of liquid permeable porous material nearer the said first chamber to act as a flow control means.

Preferably the said first chamber encloses a separate container means for liquid material to be pumped said second container means having deformable walls and communicating with the exterior of the said first chamber, whereby build-up of pressure on osmosis pump liquid from the said separate container means.

This separate container, or indeed the second chamber, can be a flexible impervious synthetic polymeric sac.

While it is intended to cover the pump per se, the filled pump, that is to say the pump as defined above and charged with an osmotically stronger solution in the first chamber and an osmotically weaker solution, or pure solvent, in the second chamber is also an aspect of the invention The osmotic solution can be any inorganic (e.g. $MgSO_4$) or organic (e.g. sucrose) water-soluble material of high osmotic activity. It is preferred however, if the osmotically stronger solution is an aqueous solution of a water-soluble polymeric material such as polyethylene glycol. Water is the most conveniently osmotically weaker pure solvent.

The flow control means can be a multi-layer structure. A wide range of material and synthetic materials (e.g. paper, fabric, porous ceramic, gels, dialysis membrane material, gelatine impregnated sponge) have been tried and are possible materials but for uniformity of behaviour and ease of handling layers of synthetic polymeric porous material are preferred.

Valuable specific products are face-to-face contiguous discs of porous polyethylene, preferably from 1 to 4 mm thick and on average with pores 10 to 100 microns across.

In a preferred construction the communicating duct is formed in the wall of the said first chamber to receive the said discs, and wherein a membrane assembly is peripherally sealingly clamped over the said duct by clamping means adapted to mount said second chamber.

The invention will be further described with reference to the accompanying drawings, in which:

FIG. 1 is a longitudinal section through an osmotic pump according to the invention.

FIG. 2 is an exploded version, also in longitudinal section, of part of the osmotic pump as shown in FIG. 1 but on a larger scale, FIG. 3 shows diagrammatically a drop-counting device for measuring the flow rate from the osmotic pump shown in FIGS. 1 and 2.

Figure 4:
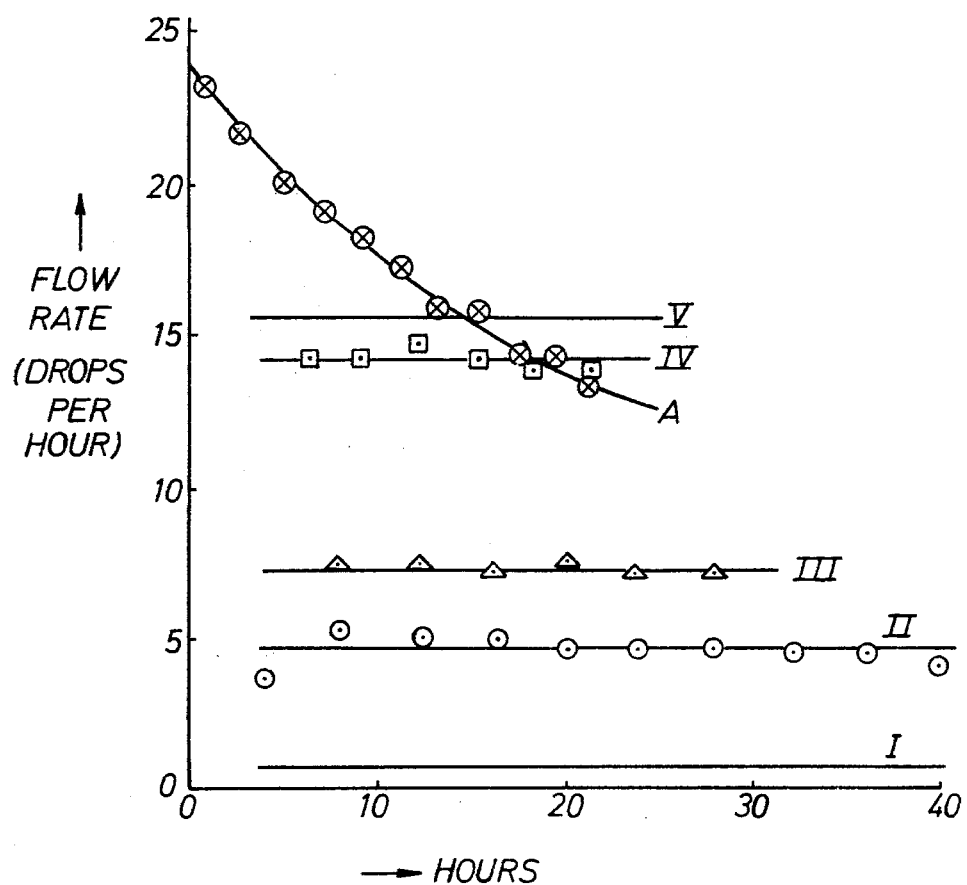
FIG. 4 is a graph of flow rates against elapsed time comparing different examples of the invention to a prior art construction.

The osmotic pump according to the invention consists generally of a rigid impervious container 1, a semi-permeable membrane and flow control arrangement 2 located at one end of the container, (the essential features of which arrangement are shown in enlarged and exploded section in FIG. 2), a collapsable bag of polymeric material 3 attached to the membrane and flow control arrangement 2, and a further collapsable synthetic polymeric bag 4 located within container 1.

Container 1 is provided at one end with a filling port 5 and a dispensing port 6. Filling port 5 enables the container to be filled through tubing 7 with an osmotic working fluid, which can for example be sucrose, although bacterial contamination is a danger or can be a high molecular weight water-soluble organic compound such as polyethylene glycol, or possibly an inorganic salt such as magnesium sulphate. Tubing 7 is clamped at 8 after the container is filled. Dispensing port 6 is provided with dispensing tube 9 on the outside and an internal extension 6a which provides a suitable fitting for the internal impervious flexible synthetic polymeric bag 4.

At the other end the container 1 is provided with a inlet passage 10 in which are located the flow control means as described in more detail below.

The semi-permeable membrane and flow-control arrangement is shown diagrammatically in FIG. 1 but can be seen in more detail in the enlarged section of FIG. 2. In this figure there is clearly shown the flow-control arrangement comprising a plurality of porous discs 11 press-fitted into the duct 10. There is also shown the semi-permeable membrane construction which is held between the end of container 1 and a separate clamping member 12 terminating in bush 12a to support the end of the flexible impervious synthetic polymeric bag 3. The clamping member 12 and the end of container 1 are firmly held together by deformable fixing ring 13 which fits into complementary slot 14 in the clamping member. When these two members are fixed in this way, they clamp the semi-permeable membrane assembly which consists successively, from the container side, of a sealing O-ring 15, the semi-permeable membrane itself 16, a pad 17 of foam rubber with intercommunicating cells, a second sealing O-ring 18, and a support gauze 19 of suitable gauge wire. Lips 10a actually bear upon the membrane 16 and foam pad 17 to provide a sharply defined membrane area.

The flexible impervious synthetic polymeric bags or envelopes 3 and 4 respectively contain a pure solvent (or at least osmotically weaker solution than that contained in container 1) and the liquid medium to be dispensed.

In use an osmotic pressure is generated across the semi-permeable membrane 16 and controlled by the flow-controlling porous discs 11. By some means which cannot be fully elucidated, the build-up of pressure in the container 1 is essentially uniform and the pressure upon flexible sac 4 which dispenses liquid out of tubing 9 leads to a uniform rate of dispensing.

FIG. 3 shows diagrammatically equipment for measuring the rate of dispensing, as used in the numerical examples given below. It consists of a container in the form of a large test tube 20 having a rubber band 21 provided with two through capillary tubes 22 and 23. Tube 22 is connected to tubing 9, while tube 23 acts as an air vent.

The purpose of allowing drop formation within the test tube 20 is to control evaporation, since drop formation is in any case slow and could be affected by evaporation from the surface of the drop. The dispensed drops of liquid 24 eventually fall from the end of capillary tube 22 and interupt a beam of light normally passing from lamp 25 to photocell 26 through the aligned slits 27 and 28 respectively. This interruption gives a measurable pulse which can be recorded on an automatic counter. For convenience the dispensed liquid accumulates in the base of the test tube, at 29, and helps to equilibrate the humidity within the test tube so that low drop rates, even down to one or two drops per hour, are not unduly affected by drop surface evaporation.

The invention will be still further described with reference to the following example of operation which specifies by way of example only certain materials, dimensions, and operating procedures.

EXAMPLE (a) Constructional Details (i) Outer container 1—60 cm$^3$ internal volume
(ii) Polymeric sac 4—9 cm$^3$ volume, polyvinyl chloride.
(iii) Polymeric sac 3—12 cm$^3$ volume, polyvinyl chloride.
(iv) Discs 11—four face-to-face press-fitted porous polyethylene discs each 2 mm thick and with 50—micron average pore size (Gallenkamp SHC-250-Q)
(v) Membrane 16—cellulose acetate available from Cornwell Products under catalogue No. DDS 999 placed with active side towards interior of container 1
(vi) Gap between membrane 16 and discs 11—0.5 mm
(vii) Capillary 22—a 21 gauge needle fitted with a small bore piece of polytetrafluoroethylene tubing, yielding a 0.025 cm$^3$ drop (b) Operational Liquids (i) In container 1—Polyethyleneglycol-400 solution in a strength of 150 cm$^3$ P.E.G. to 1 liter water.
(ii) In polymeric sac 4—water to be pumped, containing dissolved dyestuff to facilitate counting drops per hour.
(iii) In polymeric sac 3—de-ionised water.

(c) Procedural Steps (i) Polymeric sac 4 is filled by a syringe and outlet tube 9 clamped,
(ii) Discs 11 are press-fitted into duct 10,
(iii) The above assembly is immersed in a quantity of the osmotic fluid (P.E.G. solution) in a beaker and subjected to low pressure to remove internal air bubbles and impregnate the discs,
(iv) The impregnated assembly is placed with duct 10 uppermost, O-ring 15 placed in position and P.E.G. solution of the same strength is used to fill the space above the discs, (v) The membrane is placed over the filled gap with its active side inwards, care being taken to exclude air bubbles (vi) foam rubber pad 17 is filled with de-ionised water and placed against the outward face of the membrane (vii) O-ring 18 and gauze 19 are placed in position on holder 12, and clicked into place over the membrane, (viii) Polymeric sac 3 is filled with de-ionised water by means of a filling port (not shown) which is then clamped off, (ix) The main solution chamber is then filled with the P.E.G.-400 osmotic fluid, through filling port 5 and thereafter closed at 8.

(x) For reproducible results the whole unit is immersed in a constant temperature bath (24.5° C.), in the vertical orientation shown in FIG. 1, and the tubing from port 6 to the drop counter is arranged to provide one of two known hydrostatic heads of 1420 and 2480 mm of water respectively.

(d) Variants of Construction and Operation (i) Materials of Discs
Generally equivalent results were obtained using other porous materials such as filter paper, porous gels, dialysis membrane material, gelatine, impregnated sponge, or porous ceramic discs, but porous polymer e.g. polyethylene discs are much the easiest to handle and assemble.
Moreover, a comparison test was run using no porous discs, results are discussed below.

(ii) Polymeric sac 4 could be charged by first filling container 1 and then connecting the sac 4 to a source of liquid and running out some of the liquid in the container. Of course the container could be made in two detachable parts to facilitate replacement of sac 4 as necessary.

(iii) A rupturable of otherwise removable water-impervious barrier could be provided between the semi-membrane and the osmotic solution so that the device could be started up some time after assembly, (iv) The spacing between the semi-permeable membrane 16 and the nearest of discs 11 is preferably small, i.e., of the order of 0.5 mm, but larger gaps (3 mm.) have been tried, to see the effect on pumping activity.

(v) The semi-permeable membrane area can be varied between wide limits, circular membranes from 10 to 20 mm diameter being preferred. As described below, flow rates are not clearly directly proportional to membrane area.

(vi) Instead of preliminary soaking of the discs 11 in osmotic fluid, certain experiments have been carried out with the discs previously impregnated with water (and the gap between the membrane and discs also being filled with water). Results are shown and discussed below.

(vii) The hydrostatic head was set at one of two levels, with no marked difference in results.

RESULTS

All of the following results were obtained by the procedure described in the main example above, except where otherwise indicated. Note that, 2 in the Table (i) In the first column "P" indicates that the polyethylene discs were soaked in and covered with P.E.G. 400 solution as described. "W" indicates that they were soaked in and covered with de-ionised water (ii) In the second column "S" indicates a small 0.5 mm gap between the semi-permeable membrane and "L" a large 3 mm gap.

(iii) In the third column, membrane diameters are
I—10.0
II—12.5
III—15.0
IV—17.5
V—19.0,
measured in millimeters.

(iv) In the fourth column "H" indicates a higher hydrostatic pressure of 2480 mm $H_2O$, and "L" a lower of 1420 mm $H_2O$.

(v) The first numerical column shows the number of expired minutes until the first 0.025 $mm^3$ drop is pumped out.

(vi) Successive numerical columns shown
(a) Nos. 1 and 2, hours regarding successive drops
(b) Nos. 3 to 8, number of drops per successive two hour periods
(c) Nos. 9 to 33, number of drops per successive hour.

TABLE

| NO | TYPE | | | | TIME 1ST DROP | HOURS FOR SUCCESSIVE DROPS (1 AND 2) DROPS PER SUCCESSIVE HOURS (REMINDER) | | | | | | | |
|---|---|---|---|---|---|---|---|---|---|---|---|---|---|
| 1 | P | S | I | H | 195 | 2.6, | 1.9, | 1.9, | 1.6, | 1.6, | .6 | | |
| | | | | | | 1.6, | 1.6, | 1.5, | 1.6, | 1.6, | 1.8, | 1.6 | |
| | | | | | | 1.8, | 1.7, | 1.6, | 1.5, | 1.5, | 1.6, | 1.5, | 1.6 |
| | | | | | | 1.7, | 1.6, | 1.6, | 1.6, | 2.0, | 1.9, | 1.6 | |
| 2 | P | S | I | L | 720 | 2.3, | 2.0, | 2.2, | 2.0, | 2.2, | 2.2, | | |
| | | | | | | 2.0, | 2.0, | 2.0, | 1.9, | 2.0, | 1.9 | | |
| | | | | | | 2.0, | 2.0, | 2.1, | 2.1, | 2.2, | | | |
| 3 | P | S | II | H | 80 | — 7 — 7 — 7 — 8 — 8 — 10 | | | | | | | |
| | | | | | | — 10 — 11 — 10 — 10 — 10 — 9 | | | | | | | |
| | | | | | | — 10 — 10 — 9 — 10 — 9 — 9 | | | | | | | |
| | | | | | | — 9 — 10 — 9 — 8 — 8 | | | | | | | |
| 4 | P | S | II | H | 90 | — 7 — 8 — 9 — 9 — 9 — 9 | | | | | | | |
| | | | | | | — 9 — 9 — 9 — 9 — 8 — 9 | | | | | | | |
| | | | | | | — 9 — 9 — 8 — 9 — 9 — 8 | | | | | | | |
| | | | | | | — 9 — 8 — 9 — 8 — 8 — 9 | | | | | | | |
| | | | | | | — 8 — 8 — 8 — 8 — 8 | | | | | | | |
| 5 | P | S | II | H | 60 | — 9 — 7 — 8 — 8 — 8 — 9 | | | | | | | |
| | | | | | | — 8 — 8 — 8 — 8 — 8 — 7 | | | | | | | |
| | | | | | | — 8 — 7 — 8 — 7 — 8 — 7 | | | | | | | |
| | | | | | | — 8 — 7 — 8 — 7 — 7 | | | | | | | |
| 6 | P | S | II | L | 30 | — 8 — 12 — 11 — 12 — 11 — 10 | | | | | | | |
| | | | | | | — 11 — 11 — 10 — 10 — 10 — 9 | | | | | | | |

TABLE-continued

| | | | | | | | | | | | | | | | | |
|---|---|---|---|---|---|---|---|---|---|---|---|---|---|---|---|---|
| 7 | P | S | II | L | 70 | — | 10 | — | 9 | — | 10 | — | 9 | — | 10 | — | 9 |
| | | | | | | — | 10 | — | 9 | — | 10 | — | 9 | — | 9 | | |
| | | | | | | — | 9 | — | 10 | — | 10 | — | 9 | — | 10 | — | 9 |
| | | | | | | — | 9 | — | 9 | — | 8 | — | 8 | — | 8 | — | 8 |
| | | | | | | — | 8 | — | 8 | — | 8 | — | 8 | — | 8 | — | 8 |
| | | | | | | — | 7 | | | | | | | | | | |
| 8 | W | L | II | L | 120 | — | 9 | — | 10 | — | 10 | — | 10 | — | 9 | — | 10 |
| | | | | | | — | 9 | — | 10 | — | 9 | — | 9 | — | 9 | — | 9 |
| | | | | | | — | 9 | | | | | | | | | | |
| 9 | P | S | III | H | 60 | 6 | 7 | 7 | 8 | 7 | 7 | 8 | 7 | 7 | 8 | 7 | 7 |
| | | | | | | 7 | 7 | 7 | 7 | 7 | 7 | 7 | 7 | 7 | 7 | 7 | 7 |
| | | | | | | 7 | 6 | 7 | 7 | 7 | 7 | 7 | 6 | 7 | 7 | 7 | 7 |
| | | | | | | 6 | 7 | | | | | | | | | | |
| 10 | P | S | III | H | 80 | 8 | 7 | 7 | 8 | 7 | 7 | 8 | 7 | 7 | 7 | 8 | 7 |
| | | | | | | 7 | 7 | 7 | 7 | 7 | 7 | 7 | 7 | 7 | 7 | 7 | 6 |
| | | | | | | 7 | 6 | 7 | 6 | 7 | 6 | 7 | 6 | 7 | 6 | 7 | 6 |
| | | | | | | 7 | 6 | | | | | | | | | | |
| 11 | P | S | III | L | 20 | 8 | 9 | 8 | 9 | 8 | 9 | 8 | 8 | 8 | 8 | 7 | 8 |
| | | | | | | 8 | 8 | 8 | 8 | 8 | 8 | 8 | 7 | 8 | 8 | 8 | 7 |
| | | | | | | 8 | 8 | 8 | 7 | 8 | 8 | 7 | 8 | 7 | 8 | | |
| 12 | P | S | III | L | 60 | 7 | 7 | 6 | 7 | 6 | 7 | 6 | 7 | 6 | 6 | 7 | 6 |
| | | | | | | 7 | 6 | 6 | 7 | 6 | 6 | 6 | 7 | 6 | 6 | 7 | 6 |
| | | | | | | 6 | | | | | | | | | | | |
| 13 | P | S | III | L | 40 | 7 | 7 | 7 | 7 | 7 | 8 | 7 | 8 | 8 | 8 | 8 | 7 |
| | | | | | | 8 | 8 | 8 | 7 | 8 | 7 | 7 | 8 | 7 | 8 | 7 | 7 |
| | | | | | | 8 | 7 | 7 | 7 | 7 | 7 | 7 | 6 | 7 | 6 | | |
| 14 | P | S | IV | L | 10 | 14 | 16 | 16 | 16 | 15 | 16 | 15 | 15 | 14 | 15 | 14 | 14 |
| | | | | | | 15 | 14 | 14 | 14 | 14 | 14 | 13 | 13 | 12 | | | |
| 15 | P | S | IV | L | 0 | 12 | 12 | 13 | 13 | 14 | 14 | 14 | 15 | 14 | 14 | 15 | 14 |
| | | | | | | 13 | 14 | 13 | 14 | 13 | 13 | 12 | 13 | 12 | 12 | | |
| 16 | P | S | IV | L | 50 | 8 | 9 | 11 | 12 | 12 | 12 | 13 | 14 | 13 | 13 | 14 | 13 |
| | | | | | | 13 | 14 | 13 | 13 | 13 | 13 | 13 | 13 | 13 | | | |
| 17 | P | S | IV | L | 30 | 13 | 12 | 13 | 13 | 14 | 14 | 14 | 15 | 15 | 14 | 14 | 15 |
| | | | | | | 14 | 14 | 14 | 14 | 13 | 14 | 13 | 13 | 13 | | | |
| 18 | P | S | IV | L | 0 | 7 | 11 | 16 | 17 | 16 | 16 | 16 | 16 | 15 | 15 | 16 | 15 |
| | | | | | | 15 | 15 | 15 | 15 | 14 | 14 | 14 | 13 | | | | |
| 19 | P | S | IV | L | 0 | 6 | 10 | 13 | 15 | 15 | 15 | 15 | 15 | 16 | 15 | 15 | 16 |
| | | | | | | 15 | 15 | 15 | 15 | 15 | 14 | 15 | 14 | 14 | | | |
| 20 | P | S | IV | L | 60 | 11 | 12 | 13 | 13 | 13 | 13 | 14 | 14 | 14 | 13 | 14 | 14 |
| | | | | | | 13 | 14 | 13 | 13 | 13 | 14 | 13 | 14 | 13 | | | |
| 21 | P | S | IV | L | 0 | 10 | 12 | 13 | 13 | 14 | 13 | 13 | 13 | 13 | 13 | 13 | 12 |
| | | | | | | 13 | 12 | 13 | 12 | 12 | 12 | 11 | 12 | 11 | 12 | 11 | |
| 22 | P | S | IV | H | 20 | 11 | 13 | 12 | 12 | 13 | 13 | 13 | 14 | 13 | 13 | 13 | 14 |
| | | | | | | 14 | 12 | 13 | 13 | 12 | 12 | 12 | 12 | 12 | | | |
| 23 | P | S | IV | H | 15 | 10 | 11 | 14 | 14 | 14 | 15 | 14 | 14 | 15 | 14 | 14 | 14 |
| | | | | | | 13 | 14 | 13 | 14 | 13 | 12 | 13 | 12 | 13 | | | |
| 24 | P | S | IV | H | 30 | 8 | 12 | 12 | 13 | 13 | 13 | 13 | 14 | 14 | 13 | 14 | 13 |
| | | | | | | 14 | 13 | 14 | 13 | 13 | 12 | 13 | 12 | 13 | 12 | 12 | |
| 25 | P | L | IV | H | 5 | 19 | 13 | 9 | 9 | 10 | 11 | 10 | 11 | 11 | 11 | 11 | 11 |
| | | | | | | 11 | 11 | 10 | 11 | 10 | 11 | 10 | 10 | | | | |
| 26 | P | L | IV | L | 5 | 17 | 11 | 9 | 10 | 11 | 11 | 10 | 11 | 10 | 10 | 10 | 10 |
| | | | | | | 10 | 10 | 9 | 9 | 9 | 10 | 9 | 8 | | | | |
| 27 | W | L | IV | H | 90 | 8 | 9 | 9 | 10 | 9 | 9 | 10 | 9 | 9 | 8 | 9 | 9 |
| | | | | | | 9 | 10 | 9 | 9 | 9 | 9 | 8 | 9 | 9 | | | |
| 28 | W | L | IV | H | 90 | 12 | 12 | 13 | 13 | 14 | 13 | 13 | 13 | 13 | 12 | 13 | 12 |
| | | | | | | 13 | 12 | 12 | 12 | 12 | 12 | 12 | 11 | 11 | 11 | | |
| 29 | W | L | IV | L | 90 | 8 | 9 | 10 | 9 | 10 | 11 | 10 | 11 | 11 | 11 | 10 | 11 |
| | | | | | | 10 | 10 | 9 | 10 | 9 | 9 | 9 | 9 | | | | |
| 30 | W | L | IV | L | 60 | 12 | 13 | 14 | 14 | 14 | 14 | 14 | 13 | 13 | 12 | 13 | 12 |
| | | | | | | 13 | 12 | 12 | 13 | 12 | 12 | 11 | 11 | 12 | 11 | | |
| 31 | P | S | V | L | 80 | 16 | 15 | 16 | 16 | 16 | 16 | 17 | 16 | 16 | 16 | 16 | 16 |
| | | | | | | 15 | 16 | 15 | 15 | 15 | 15 | | | | | | |
| 32 | P | S | V | L | 70 | 7 | 12 | 14 | 13 | 13 | 14 | 14 | 14 | 14 | 14 | 14 | 14 |
| | | | | | | 14 | 13 | 14 | 14 | 14 | 13 | 14 | | | | | |
| 33 | W | L | V | L | 120 | 13 | 14 | 15 | 14 | 15 | 14 | 14 | 14 | 14 | 13 | 14 | 13 |
| | | | | | | 13 | 14 | 13 | 13 | 13 | 13 | 13 | | | | | |

The graph of FIG. 4 illustrates features from these results. For each membrane I to V the average flow rate in drops per hour after specified periods has been calculated from comparable results in the table. Thus, for membrane II the results of experiments 6 and 7 have been averaged, for membrane III those of experiments 11, 12, and 13, and for membrane IV those of experiments 14 to 21. There are no strictly comparable repeated experiments for membranes I and V, but the indicated lines in the graph show the general native of the results.

From this graph it is readily apparent:

(a) That the flow rates of the osmotic pump according to the invention are generally constant over useful periods of time, and can be adjusted generally by alterations of membrane area.

(b) That measured membrane area itself is not however strictly linear with flow rate, possibly indicating some unexpected physiochemical behaviour at the membrane.

(c) That comparison of the uniform flow rates according to the invention with the curve A (showing flow rates with an identical osmotic pump with membrane III but omitting the porous discs) indicates that:

(i) Overall flow rates are considerably reduced by the porous discs, (ii) The decrease in flow rates of curve A is much greater than any overall decrease in strength of the osmotic solution, (iii) The decrease in flow rate of curve A is much greater than would be anticipated in that solvents diffused through the membrane would be expected to rise by its lower specific gravity and thus draw in stronger osmotic fluid to contact the membrane and thereby keep the flow rate up. This again possibly indicates some unexpected physiocochemical behaviour at the membrane.

It is also apparent, from consideration of the results in the above table that:

(a) The majority of the experiments use discs pre-impregnated with P.E.G. solution only a short distance from the membrane. it is difficult to generalise, but usually this leads to a time lag of up to 1½ hours before the first drop, and fairly steady flow thereafter. The reasons for the time lag are not clear.

(b) In experiments 25 and 26 the P.L condition (using P.E.G. to soak the discs and fill a large disc-to-membrane gap) gives a generally quicker start (presumably because P.E.G. is already at the membrane) but a high flow rate for the first hour or so, which later settles to a lower steady rate.

(c) In experiments 8, 27-30 and 33 the W.L condition increases the starting time to usually over 1½ hours, presumably because the P.E.G. has first to diffuse through the discs to arrive at the membrane.

(d) A large disc-to-membrane gap eventually gives generally equivalent steady flow rate values to those of a small disc-to-membrane gap (e) Large or small hydrostatic heads (to the extent specified) affect the flow rate only slightly if at all (f) Steady flow rates from 0.25 to 9.0 cm$^3$ per day are attainable.

It will be apparent therefore that the device specifically described above is self-contained, can be made small enough to be worn by ambulatory patients, gives a steadier supply of active agent than normally associated with tablets, capsules, injections, etc, and may also find use in other situations where small volumes must be steadily pumped e.g. in feeding nutrient solutions into a culture medium.

While the Applicants do not wish to be limited, within the scope of the invention as defined in the appended claims, to any theory as to the operation of this pump, it seems possible that the rate of diffusion of stronger osmotic fluid through the porous discs corresponds to that of the weakening of the arriving fluid by osmotic transfer across the semi-permeable membrane, so that the membrane is generally in a more controlled environment than if the dilution products were allowed to convect or wash away in an arbitrary fashion.

I claim:

1. An extracorporeal osmotic pump comprising a first chamber for containing an osmotically stronger solution; a second chamber for containing an osmotically weaker solution or pure solvent; a duct located between the said chambers placing them in communication; a semi-permeable membrane across said duct located nearer the said second chamber; and at least one layer of liquid-permeable porous material across said duct located nearer the said first chamber, whereby it acts as a flow-control means.

2. An extracorporeal osmotic pump as claimed in claim 1 further comprising: separate container means located within said first chamber for containing liquid material to be pumped, said container means having deformable walls and an outlet means placing in communication the exterior of the said first chamber, and the interior of the said container means, whereby build-up of pressure on osmosis pumps liquid from the said separate container means.

3. An entracorporeal osmotic pump as claimed in claim 2 wherein said separate container means is a flexible impervious synthetic polymeric sac.

4. An extracorporeal osmotic pump as claimed in claim 1 wherein said second chamber is a flexible impervious synthetic polymeric sac.

5. An osmotic pump as claimed in claim 1 in which the flow control means is a multi-layer structure.

6. An osmotic pump as claimed in claim 5 in which the flow control means consists of a plurality of layers of synthetic polymeric porous material.

7. An osmotic pump as claimed in claim 6 in which the flow control means consists of a plurality of face-to-face contiguous discs of porous polyethylene.

8. An osmotic pump as claimed in claim 7 wherein said discs of porous polyethylene are each 1 to 4 mm thick with pores on average 10 to 100 microns across.

9. An osmotic pump as claimed in claim 7 wherein the communicating duct is formed in the wall of the said first chamber to receive the said discs; further comprising a membrane assembly peripherally sealingly clamped over the said duct by clamping means adapted to mount said second chamber.

10. An extracorporeal osmotic pump comprising a first chamber charged with an osmotically stronger solution; a second chamber charged with an osmotically weaker solution or pure solvent; a duct located between the said chambers placing them in communication; a semi-permeable membrane across said duct located nearer the said second chamber; and at least one layer of liquid-permeable porous material across said duct located near the said first chamber, whereby it acts as a flow control means.

11. An extracorporeal osmotic pump as claimed in claim 10 charged in the first chamber with an aqueous solution of a water soluble polymeric material.

12. An extracorporeal osmotic pump as claimed in claim 11 charged in the first chamber with an aqueous solution of a polyethylene glycol and in the second chamber with deionized water.

* * * * *